United States Patent
Naarup (10) Patent No.: US 8,062,589 B2
(45) Date of Patent: *Nov. 22, 2011

(54) ADJUSTABLE UV AIR PURIFIER

(75) Inventor: Gary Naarup, Green Bay, WI (US)

(73) Assignee: Premier One Products, Pulaski, WI (US)

( * ) Notice: Subject to any disclaimer, the term of this patent is extended or adjusted under 35 U.S.C. 154(b) by 706 days.

This patent is subject to a terminal disclaimer.

(21) Appl. No.: 11/999,612

(22) Filed: Dec. 6, 2007

(65) Prior Publication Data

US 2008/0138241 A1    Jun. 12, 2008

Related U.S. Application Data

(62) Division of application No. 10/823,255, filed on Apr. 13, 2004, now Pat. No. 7,597,856.

(51) Int. Cl.
*A61L 9/00* (2006.01)
*A61L 2/00* (2006.01)
*A61L 2/18* (2006.01)
*A62B 7/08* (2006.01)

(52) U.S. Cl. .......... 422/29; 422/5; 422/22; 422/24; 422/28; 422/120; 422/121; 422/123

(58) Field of Classification Search ............ 422/22, 422/24, 5, 28, 29, 120, 121, 123
See application file for complete search history.

(56) References Cited

U.S. PATENT DOCUMENTS

| | | | |
|---|---|---|---|
| 2,347,672 A * | 5/1944 | Dircksen et al. | 362/260 |
| 3,752,748 A * | 8/1973 | McMillan, Jr. | 204/157.5 |
| 4,992,169 A | 2/1991 | Izumiya | |
| 5,154,893 A | 10/1992 | Nakade | |
| 5,219,534 A | 6/1993 | Reynolds | |
| 5,230,220 A | 7/1993 | Kang et al. | |
| 5,326,539 A | 7/1994 | Taylor | |
| 5,334,347 A | 8/1994 | Hollander | |
| 5,601,786 A | 2/1997 | Monagan | |
| 5,755,103 A | 5/1998 | Na et al. | |
| 5,817,276 A | 10/1998 | Fencl et al. | |
| 5,839,155 A | 11/1998 | Berglund et al. | |
| 5,929,455 A | 7/1999 | Jensen | |

(Continued)

FOREIGN PATENT DOCUMENTS

JP    09169503 A  *  6/1997

OTHER PUBLICATIONS

English translation of JP 09-169503 A.*

*Primary Examiner* — Sean E Conley
*Assistant Examiner* — Regina Yoo
(74) *Attorney, Agent, or Firm* — Bose McKinney & Evans LLP; John W. Bain (57) ABSTRACT

An enclosure covers a UV lamp and has a mechanically-adjustable opening for changing an amount of the UV radiation being emitted from the enclosure, and an ozone-creating passageway receives the radiation being emitted from the enclosure. A method includes producing ozone-generating radiation, mechanically attenuating the ozone-generating radiation, and mixing the attenuated ozone-generating radiation with air to produce ozone. The method may include powering a lamp for emitting ozone-producing radiation, and adjusting an amount of ozone produced by the ozone-producing radiation by rotating a first opening with respect to a second opening.

15 Claims, 8 Drawing Sheets

U.S. PATENT DOCUMENTS

| | | |
|---|---|---|
| 6,165,816 A | 12/2000 | Mizushima et al. |
| 6,276,304 B1 | 8/2001 | Tai |
| 6,316,877 B1 | 11/2001 | Kaas |
| 6,322,614 B1 | 11/2001 | Tillmans |
| 6,426,053 B1 | 7/2002 | Barnes |
| 6,468,433 B1 | 10/2002 | Tribelski |
| 6,508,982 B1 | 1/2003 | Shoji |
| 6,514,467 B1 * | 2/2003 | Bulsink et al. ........ 422/122 |
| 6,589,476 B1 | 7/2003 | Fencl |
| 6,589,489 B2 | 7/2003 | Morrow et al. |
| 6,610,990 B1 | 8/2003 | Moruzzi |
| 7,597,856 B2 * | 10/2009 | Naarup ........ 422/121 |
| 2001/0042842 A1 * | 11/2001 | Leighley et al. ........ 250/504 H |
| 2002/0098109 A1 | 7/2002 | Nelson et al. |

* cited by examiner

ADJUSTABLE UV AIR PURIFIER

CROSS REFERENCE TO RELATED APPLICATION

This application is a divisional of U.S. application Ser. No. 10/823,255, filed Apr. 13, 2004, now U.S. Pat. No. 7,597,856, the content of which is herein incorporated by reference in its entirety.

BACKGROUND

1. Field of the Invention

The invention relates generally to photochemical processes and, more particularly, to an air purifier and method that utilize UV radiation.

2. Background of the Invention

Photochemical reactions are chemical processes initiated by absorption of energy in the form of visible, infrared, or ultraviolet radiation. Photochemistry is different from many other forms of chemistry because if an atom or molecule absorbs energy from a beam of light, it gains far more energy than it could by other methods, such as heating. Consequently, photochemical processes are extremely efficient for the conversion of energy from light into chemical energy.

Many natural processes are photochemical. Ozone is produced in nature by the action of sunlight on oxygen molecules. In the stratosphere at altitudes of about 25 km, very high-energy (very short wavelength) ultraviolet light converts diatomic oxygen (O.sub.2) into ozone (O.sub.3). In other words, sunlight breaks down some of the oxygen molecules into atoms, which combine with other oxygen molecules to produce ozone:

Such an expression is, of course, over-simplified because additional particles are typically involved that absorb some of the heat released during the process, and because ozone is quite unstable and will itself interact with light, alkenes, etc.

This tri-atomic form of oxygen formed naturally in the upper atmosphere by a photochemical reaction with solar ultraviolet radiation is commonly referred-to as the ozone layer. This protective layer absorbs harmful solar ultraviolet radiation and prevents the radiation from passing through, thereby protecting the Earth from these damaging rays. This process decomposes and neutralizes ozone which is then replaced by new ozone created by ongoing photochemical reactions. Ozone is also measured in trace amounts in the lower atmosphere and is used by Mother Nature to purify and deodorize the air.

Ultraviolet (UV) lamps may be used to create ultraviolet energy and ozone by the same photochemical process. By emitting ultraviolet rays into the air, the resultant ozone may be used for air purification. Pure ozone is very caustic and breaks down (oxidizes) any gas it comes in contact with. The target gas or substance (e.g., smoke contaminants) is broken into component parts and is destroyed. As a result, odors are removed from rooms, including those odors trapped in carpeting and drapes. Ozone used for this purpose must be replenished because the ozone molecule is unstable and decomposes after only a short time. For example, a given quantity of ozone dispersed into a room typically will completely dissipate within fifteen to twenty minutes.

Although air purification systems for generating ozone are known, such are not optimized for adaptation to different applications and/or conditions.

OBJECTS OF THE INVENTION

It is an object of the invention to provide an improved method, system and apparatus for adjusting a level of ozone generation used for purifying air, while overcoming some of the problems and shortcomings of the prior art, including those referred to above.

Another object of the invention is to provide a system and method for mechanically attenuating ozone-generating UV radiation.

Another object of the invention is to provide an optimized, yet simple and inexpensive system and method for controllably purifying indoor air using ozone.

Still another object of the invention is to provide a system and method that effectively separates a process of generating UV radiation from a subsequent use of that UV radiation for producing ozone.

Yet another object of the invention is to provide a system and method for adjustably removing bio-aerosols, volatile organic compounds, and organic and inorganic particulate from indoor air.

A further object of the invention is to provide a UV air purification system and method adaptable to being implemented in any indoor environment.

It is also an object of the invention to reduce human health problems including asthma, allergies, and other illnesses including those caused by germs and viruses, thereby reducing health care and associated costs, and improving the quality of life.

Another object of the invention is to provide an air purification system and method that is safe yet optimizes performance.

How these and other objects are accomplished will become apparent from the following descriptions and the drawings.

SUMMARY OF THE INVENTION

In an aspect of the invention, a method includes providing an ozone-generating lamp within a pair of coaxial enclosures, one of the enclosures structured for rotating with respect to the other enclosure, and providing an opening in each of the enclosures, where the degree of overlap of the openings effected by the rotating determines an amount of ozone being produced by the lamp.

According to another aspect of the invention, a method includes providing a lamp for emitting ozone-producing radiation, providing an enclosure for covering the lamp, the enclosure having a mechanically-adjustable opening for changing an amount of the radiation being emitted from the enclosure, and providing an ozone-creating passageway for receiving the radiation being emitted from the enclosure.

In a further aspect of the invention, a method includes powering a lamp for emitting ozone-producing radiation, and adjusting an amount of ozone produced by the ozone-producing radiation by rotating a first opening with respect to a second opening.

In a still further aspect of the invention, a method includes producing ozone-generating radiation, mechanically attenuating the ozone-generating radiation, and mixing the attenuated ozone-generating radiation with air to produce ozone.

In yet another aspect of the invention, apparatus includes a lamp for emitting ozone-producing radiation, first and second pipes respectively having first and second openings, the first and second pipes enclosing the lamp and being concentrically arranged with respect to one another, and an adjustment member connected to the first pipe for rotating the first opening with respect to the second opening, where the rotating is operative to adjust an amount of ozone being produced by the ozone-producing radiation.

According to an additional aspect of the invention, apparatus includes at least one lamp for emitting ozone-producing radiation, means by which a user can mechanically adjust an amount of the ozone-producing radiation being emitted, and means for receiving the amount of ozone-producing radiation being emitted.

According to still another aspect of the invention, a system includes a lamp for emitting ozone-producing radiation, an enclosure covering the lamp and having a mechanically-adjustable opening for changing an amount of the ozone-producing radiation being emitted from the enclosure, and an ozone-creating passageway for receiving the ozone-producing radiation being emitted from the enclosure.

In a still further aspect of the invention, a system includes a lamp for producing ozone-generating radiation, an attenuator for mechanically attenuating the ozone-generating radiation, and an air passageway for receiving the attenuated ozone-generating radiation and mixing the ozone-generating radiation with air to produce ozone.

There is a need for a simple and reliable system and method for allowing a user to adjust the level of ozone being produced by her air purification system. By providing such a system and method, the invention overcomes some of the problems and shortcomings of the prior art, including those referred to above. For example, by providing for mechanical attenuation of ozone-generating UV radiation, an optimized, yet simple and inexpensive system and method for controllably purifying indoor air using ozone is obtained, whereby bioaerosols, volatile organic compounds, and organic and inorganic particulate may be removed from indoor air. As a result, health effects caused by impurities in indoor air including asthma, allergies, and other illnesses such as those caused by germs and viruses, are minimized and associated health care costs are reduced.

The foregoing summary does not limit the invention, which is instead defined by the attached claims.

DETAILED DESCRIPTION OF PREFERRED EMBODIMENTS

Figure 1:
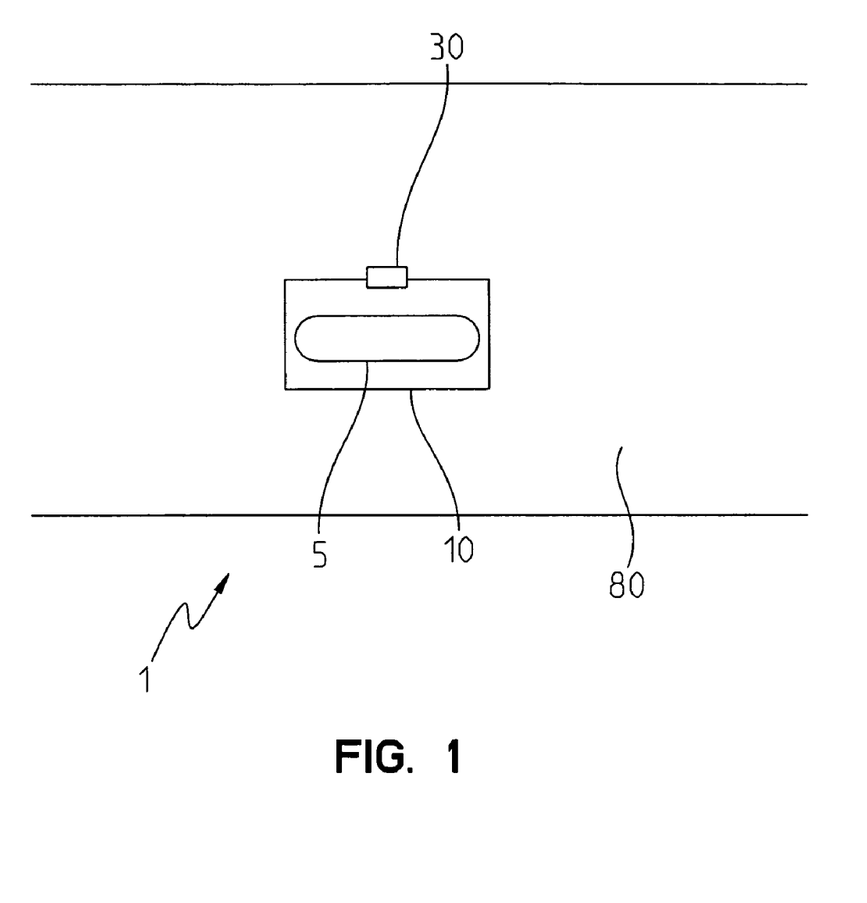
FIG. 1 is a schematic drawing of an adjustable ozone-generating type air purifier according to an exemplary embodiment of the present invention.

FIG. 1 schematically shows an exemplary system 1 according to the present invention. An ozone-generating lamp 5 is disposed within an enclosure 10. Enclosure 10 completely covers lamp 5 so that, when energized, ozone-producing radiation from lamp 5 is trapped within enclosure 10 and is not allowed to escape. A mechanism 30 is provided in a portion of enclosure 10 in order to allow a controlled portion of the radiation to escape from enclosure 10 into an airflow passageway 80. When the controlled amount of radiation is allowed to enter airflow passageway 80, a controlled amount of ozone is thereby produced. The radiation causes a photochemical process that produces ozone.

For example, lamp 5 may be a high-output ultraviolet ("UV") lamp. Ultraviolet light is measured in nanometers, and the bactericidal range is found in the shorter wavelengths of the UV spectrum. UV lamps typically used for indoor air purification emit rays with a wavelength of 185 nm and/or 253.7 nm. The former is known for being highly oxidative and useful for odor decomposition and removal, and acts to generate large amounts of ozone when exposed to air. The latter is especially useful for killing fungi and germs such as E-coli and other bacteria.

Figure 2:
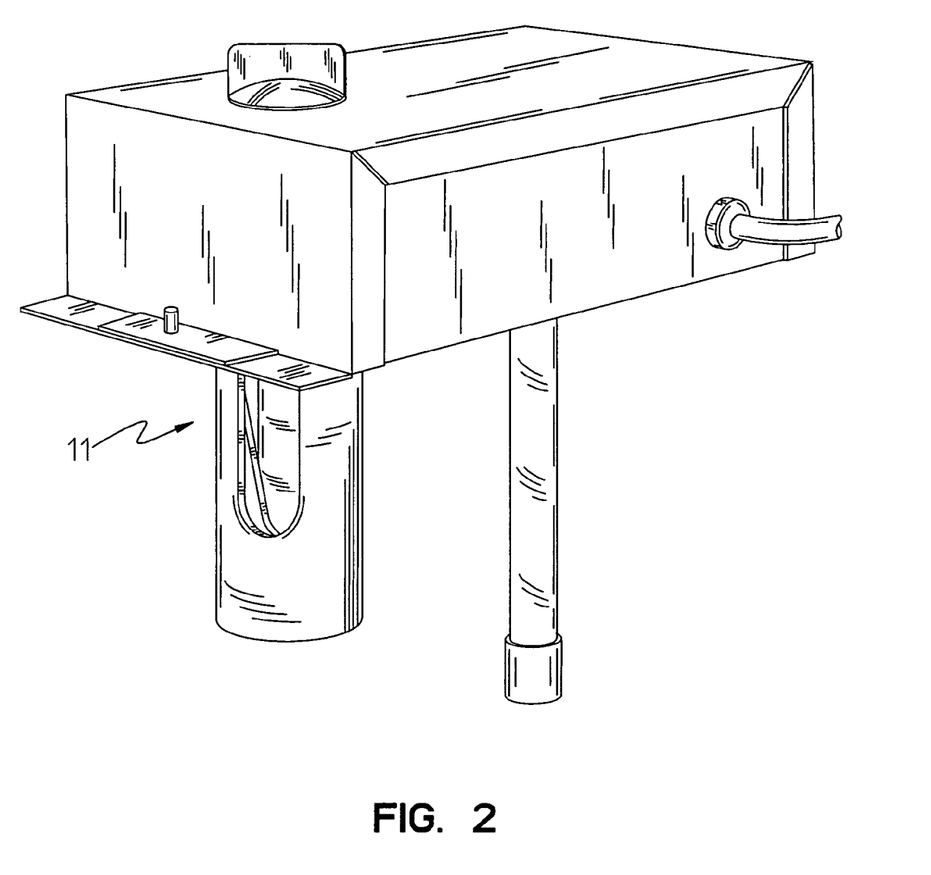
FIG. 2 is a three-dimensional view of a two-lamp ultraviolet (UV) air purification unit of a type for being mounted in a heating, ventilation and air conditioning (HVAC) duct, according to an exemplary embodiment of the present invention.

FIG. 2 is a three-dimensional view of a two-lamp ultraviolet (UV) air purification unit 11 of a type for being mounted in a heating, ventilation and air conditioning (HVAC) duct, according to an exemplary embodiment of the present invention.

Figure 3:
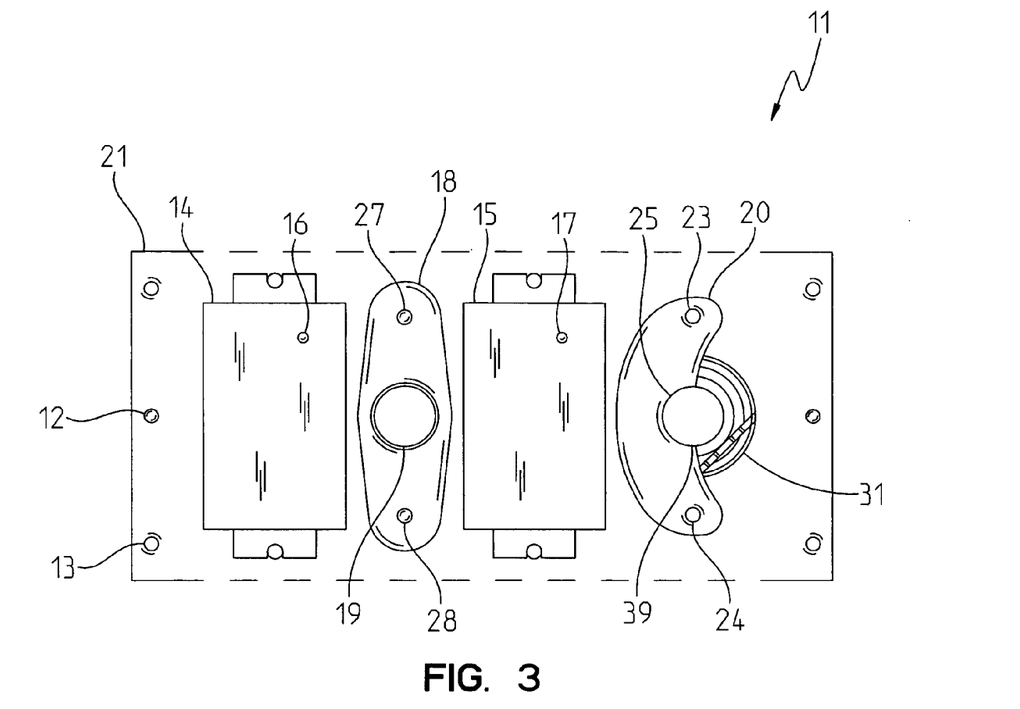
FIG. 3 is a top view (minus box cover and UV lamp assemblies) of the two-lamp ultraviolet air purification unit of FIG. 2.

FIG. 3 is a top view of two-lamp air purification unit 11 (minus box cover and UV lamps) of a type for being mounted in an HVAC duct. A base plate 21 provides surfaces for mounting an enclosure assembly 31, a first ballast 15, a second ballast 14, and a bare bulb (not shown). Ballasts 14, 15 respectively have light-emitting diodes (LEDs) 16, 17 that illuminate when power is being supplied by the particular ballast. Mounting holes 13 at each or the four corners of base plate 21 provide a means for mounting two-lamp air purification unit 11 to another structure. Studs 12 are located at the middle of both lengthwise ends of base plate 21 for mounting a top cover, described below.

Figures 4A, 4B:
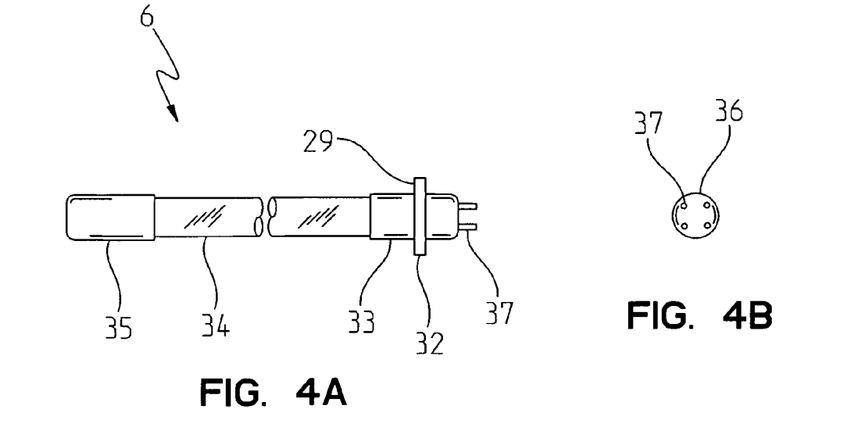
FIGS. 4A and 4B respectively show a UV lamp side view and end view, according to an exemplary embodiment of the invention.

Enclosure assembly 31 has a round opening 39 for accepting a UV bulb/lamp having a form as shown in FIGS. 4A and 4B. Such a form is represented by lamp assembly 6, which has the same general size and shape for particular bulbs 34 of different length and emission spectra. A ceramic end cap 35 is attached to the distal end of bulb 34, and a ceramic base 33 is attached to the proximal end of bulb 34. Ceramic base 33 has a flange 32 having a diameter greater than that of opening 39 of enclosure assembly 31. A diameter of the non-flange portion of ceramic base 33 is less than that of opening 39. As a result, flange 32 rests atop enclosure assembly when the UV lamp assembly is placed into opening 39. A lower bulb clamp 20 holds the UV lamp assembly in place. Similarly, a second UV lamp assembly having a same shape ceramic base 33 with a flange 32 may be placed into hole 19 of base plate 21 and upper bulb clamp 18. The assembly and structure for installing UV lamps in two-lamp air purification unit 11 is described in more detail below.

Figure 5A:
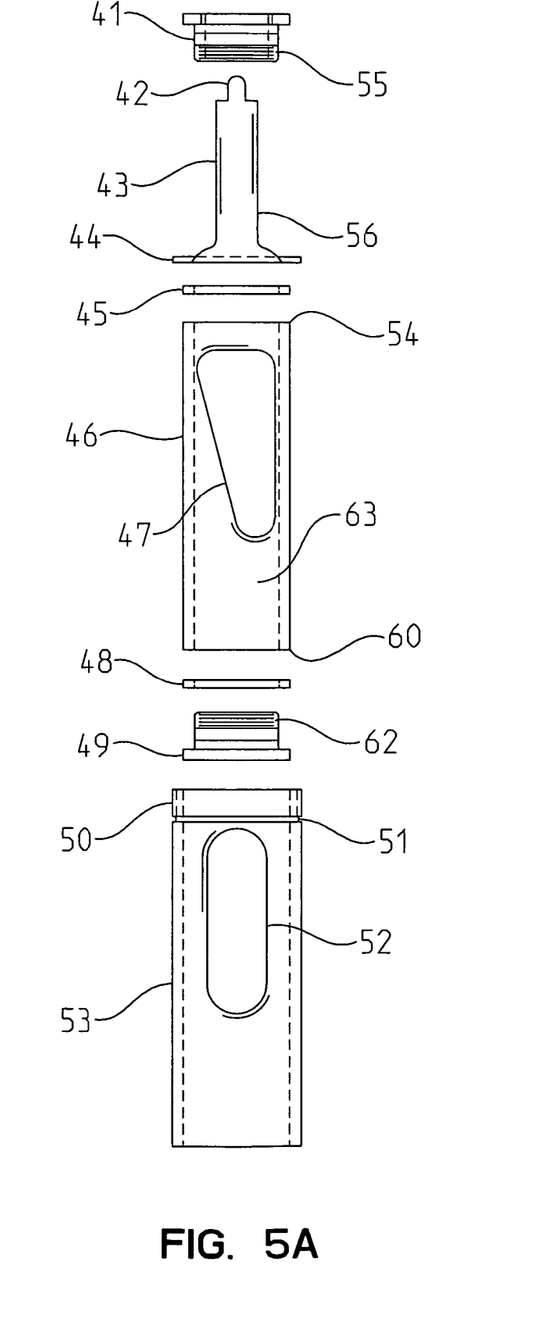
FIGS. 5A and 5B respectively show an exploded view and a partially-assembled view of an adjustable enclosure assembly of the two-lamp ultraviolet air purification unit of FIG. 2.
Figure 5B:
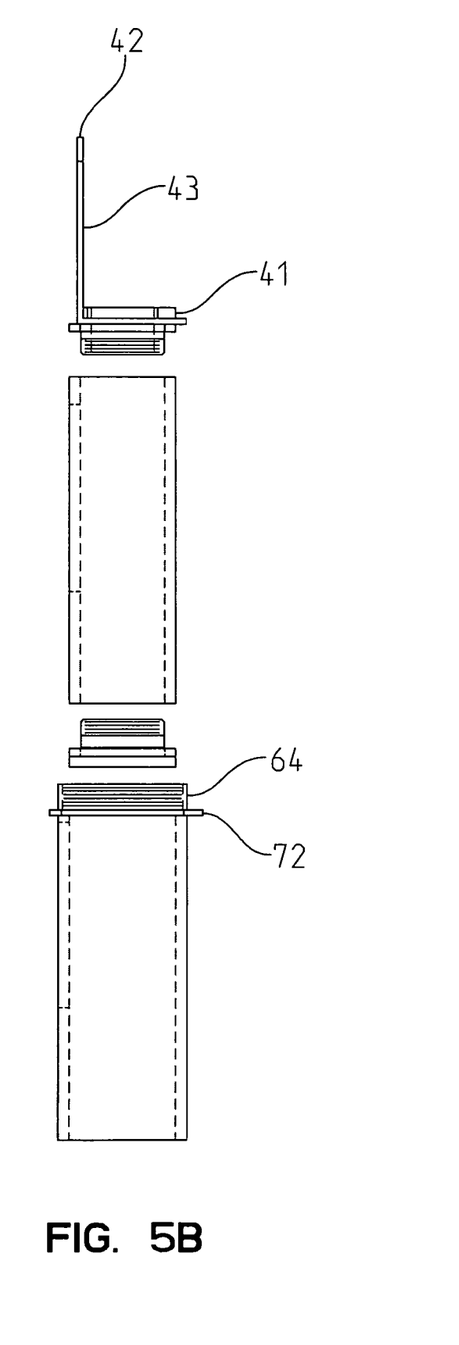
Figures 6, 7, 8:
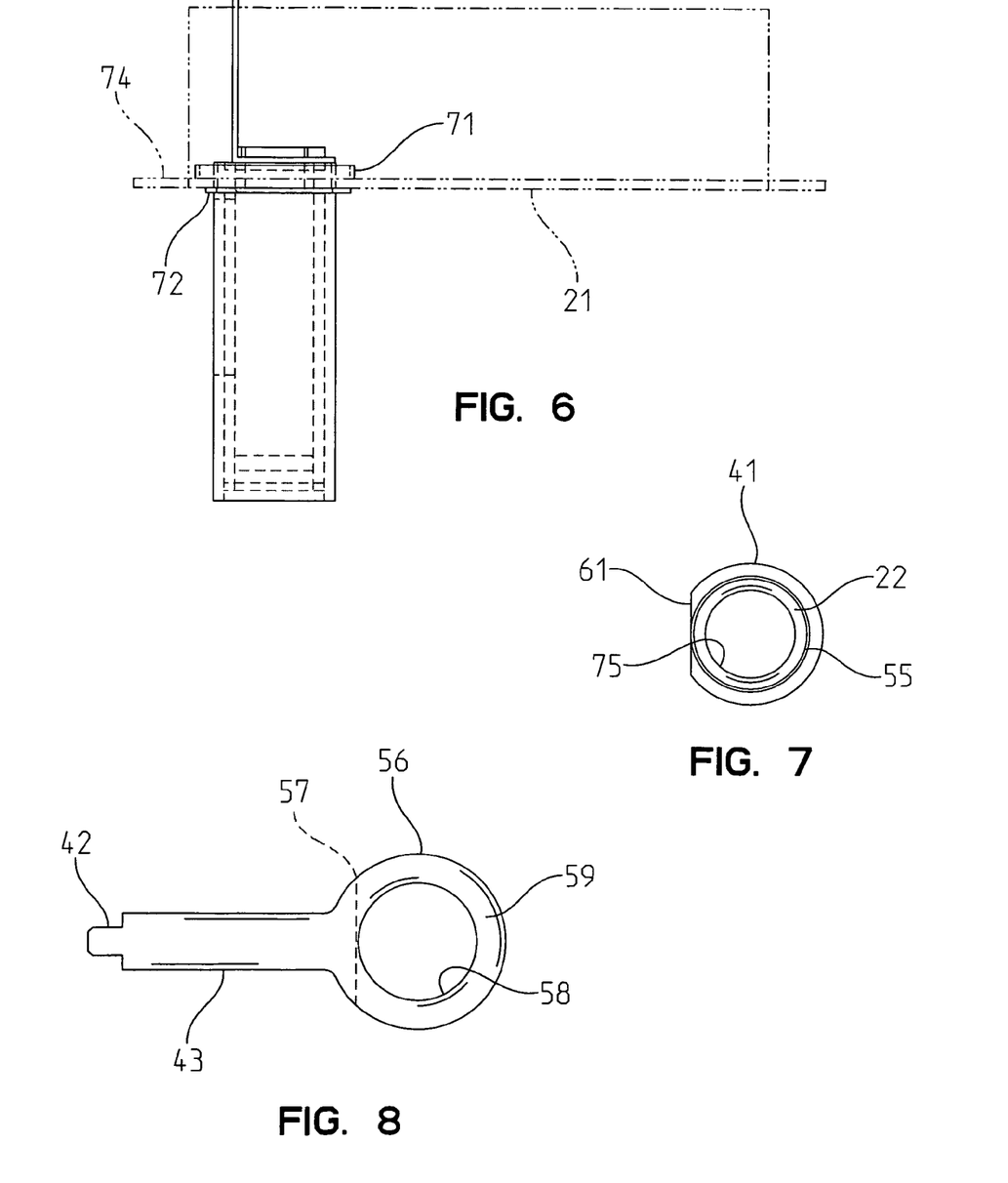
FIG. 6 shows a fully assembled adjustable enclosure assembly (less UV bulb), mounted on a base plate of a box of the two-lamp ultraviolet air purification unit of FIG. 2.
FIG. 7 shows an upper end plug of the adjustable enclosure assembly of FIGS. 5A, 5B, and 6.
FIG. 8 shows a lever of the adjustable enclosure assembly of FIGS. 5A, 5B, and 6.
Figure 9:
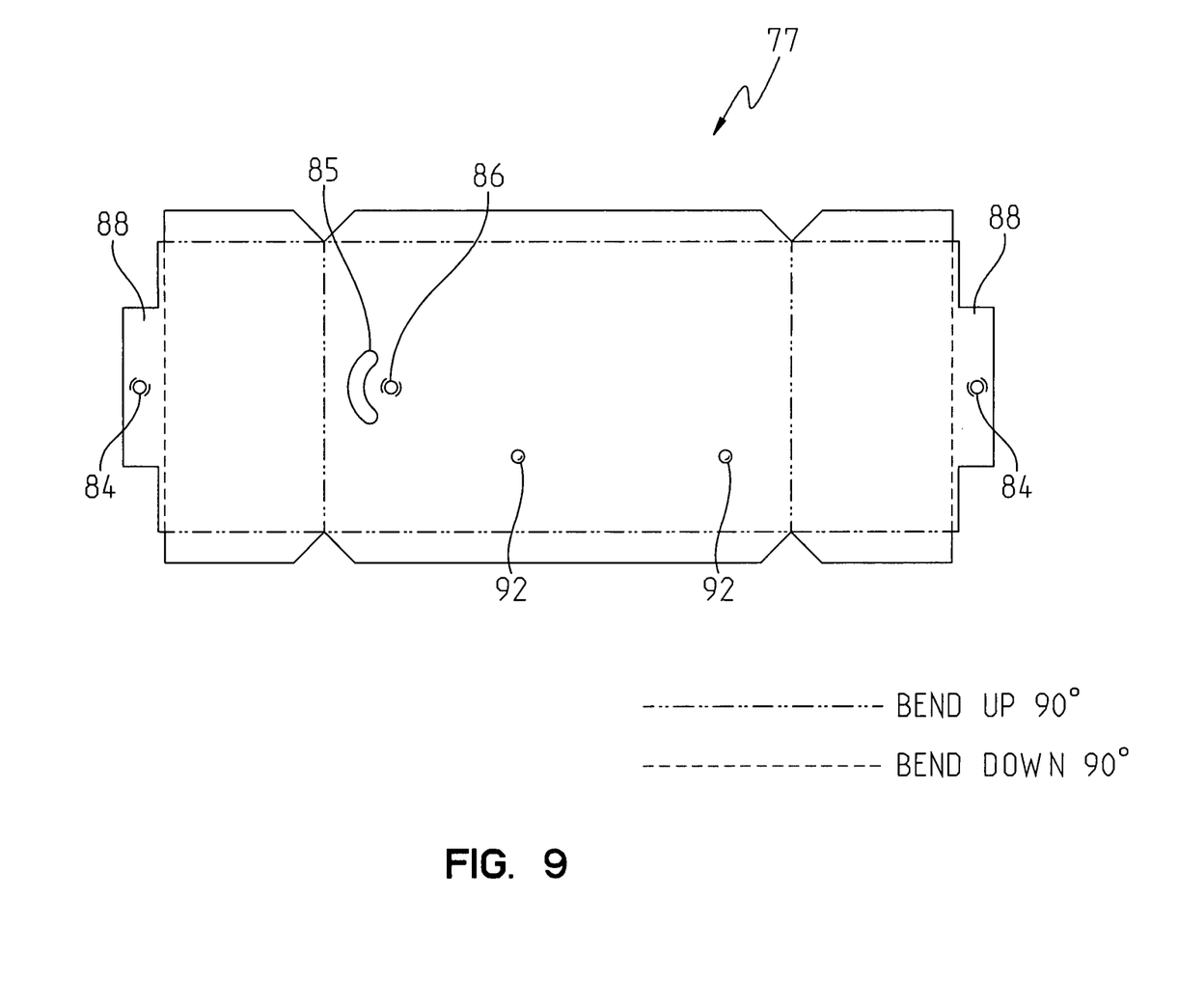
FIG. 9 shows a box lid of the two-lamp ultraviolet air purification unit of FIG. 2.

FIGS. 5A and 5B respectively show an exploded view and a partially-assembled view of an adjustable enclosure assembly 31 of two-lamp ultraviolet air purification unit 11 of FIG. 3. An inner tube 46 has an upper end 54 having inner threads (not shown) for receiving the corresponding threads 55 of upper plug 41. For example, upper plug 41 and inner tube 46 may be formed of aluminum, composite, plastic, or other suitable material. In a preferred embodiment, inner tube 46 is a Schedule 40 aluminum seamless pipe having a one inch diameter. FIG. 8 shows an exemplary lever 56. Lever 56 and a nylon washer 45 each have holes for receiving upper plug 41. In a preferred embodiment, nylon washer 45 is formed as a flanged cap that snugly fits over inner tube 46. The flanged portion extends radially beyond a mounting portion 59 of lever 56, so that mounting portion 59, which may be made of metal, is prevented from unwanted contact with external objects. Nylon washer 45 acts as a bushing to provide for smooth, low-friction rotation of inner tube 46 when inner tube 46 is installed in outer tube 53. When upper plug 41 is securely tightened into inner tube 46, lever 56 is tightly held so that an extending portion 43 projects upwards.

As shown in FIG. 7, upper plug 41 has a flat side 61 that provides an alignment surface for allowing extending portion 43 to project directly above inner tube 46, thereby saving space and allowing a knob to be attached to a distal end 42 of extending portion 43, as described below. Consistent manufacture of threads 55 assures that flat spot 61 of upper plug 41, and extending portion 43, are aligned when upper plug 41 is tightened into inner tube 46.

The lower end 60 of inner tube 46 has a threaded inner surface (not shown) for receiving the threaded end 62 of a lower plug 49 placed through a nylon washer 48. Upper plug 41 and lower plug 49 may be formed of a same material as inner tube 46, for compatibility. Nylon washer 48 extends radially beyond the outer surface of lower plug 49 and limits potential wobble of the lower end 60 of inner tube 46 by the proximity of the outside edge of washer 48 to the inner surface of outer tube 53.

An opening 47 is formed in the sidewall 63 of inner tube 46. Opening 47 may be tapered as shown in FIG. 5A to provide increased adjustment resolution (discussed further below) when adjusting the amount of UV radiation being emitted. Such a taper may have a linear profile or may have an optimized shape such as a parabolic curve.

Outer tube 53 has an opening 52 formed with a lengthwise dimension close to or the same as a lengthwise dimension of opening 47 of inner tube 46. The inside diameter of outer tube 53 is slightly larger than the diameter of nylon washer 48, so that the assembled inner tube assembly can be inserted into the outer tube 53. Although the illustrated embodiments herein show respective single openings 47, 52 in inner tube 46 and outer tube 53, multiple holes in various patterns may instead be formed in inner tube 46 and/or outer tube 53 for achieving different properties for an adjustment of radiation emission when rotating such holes respecting one another. For example, when an arrangement of holes having a pattern that radially tapers size and/or occurrence of the holes is formed in inner tube 46, additional adjustment resolution may be obtained.

Figure 10:
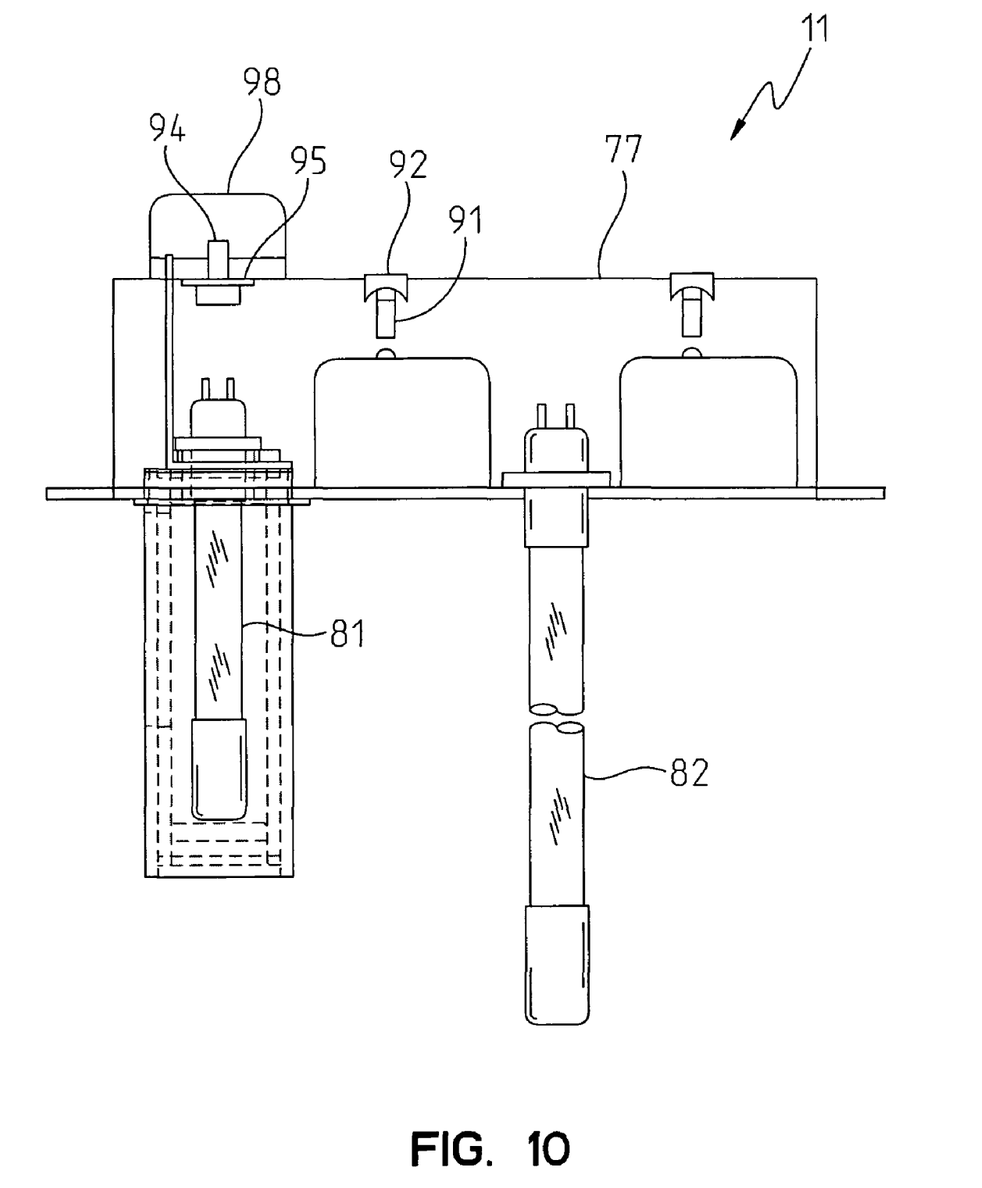
FIG. 10 is a side view showing various features of the two-lamp ultraviolet air purification unit of FIG. 2, including placement of UV bulbs.

In a preferred embodiment, the upper end 50 of outer tube 53 has male threads 64 on its outer surface so that, as shown in FIG. 6, when outer tube 53 is inserted into a hole in base plate 21, a locknut 71 is tightened onto threads 64 to secure outer tube 53 to base plate 21. As shown in FIGS. 5B, 6, and 10, a spring clip 72 is used to secure and/or stabilize the outer tube with respect to the outer side of base plate 21. Spring clip 72 is placed onto a groove 51 just below upper end 50 of outer tube 53.

After the outer tube 53 has been mounted to base plate 21, the assembled inner tube assembly is placed into outer tube 53 so that the extending portion 43 of lever 56 is positioned toward the outer lengthwise end 74 of base plate 21. Then, as shown in FIG. 10, a UV bulb assembly 81 is placed into inner tube 46 through hole 75 of upper plug 41. UV bulb assembly 81 has a form 6 such as that illustrated in FIGS. 4A and 4B, and is available from Light Sources, Inc. For example, a suitable UV bulb assembly has a Light Sources part number GPH127T5. UV bulb assembly 81 has a single-ended, four-pin, ceramic base structure. UV bulb assembly 81 has two filaments, respectively near opposite ends of bulb 34. Power is supplied individually to each of the filaments, the four pins 37 being connected, respectively, to individual sides of the two filaments. Insulated wires (not shown) extend along the outside of the UV bulb 34 from two of the pins 37 to the filament located at the distal end of assembly 81. Pins 37 are located in the proximal end 36 of UV lamp assembly 81 and have a configuration as shown in FIG. 4B.

Flange 32 extends radially from base 33, so that when assembly 81 is placed into inner tube 46, a resting surface 29 of flange 32 abuts the upper surface 22 of upper plug 41. A lower bulb clamp 20 is then placed onto standoffs and washers placed onto threaded studs (not shown) located at mounting positions 23, 24. Nuts are then tightened onto the threaded studs to secure lower bulb clamp 20 to the standoffs. The nuts are tightened to be secure and to allow the round inner portion 25 of lower bulb clamp 20 to abut flange 32f UV bulb assembly 81. Over-tightening of the nuts is avoided so that UV bulb assembly 81 is secured without preventing the free rotation of inner tube 46. In other words, if lower bulb clamp 20 presses against flange 32 with too much force, flange 32 would press against the upper surface 22 of upper plug 41 and would thereby prevent inner tube 46 from freely rotating. The diameter of the base 33 of UV bulb assembly 81 is slightly less than the inner diameter of inner tube 46, so that inner tube 46 is able to freely rotate without being appreciably affected by UV bulb assembly 81. The interface of the ceramic material of base 33 with the aluminum of upper plug 46 acts as a natural bushing, allowing UV bulb assembly 81 to remain fixed in place while inner tube 46 is being rotated. As described, a preferred embodiment is designed so that lower bulb clamp 20 securely retains UV bulb assembly 81 while simultaneously not inhibiting rotation of inner tube 46.

Alternatively, various other structures may be implemented for preventing UV bulb assembly 81 from rotating. For example, a clip may be attached to base 33 and be separately secured to lower bulb clamp 20. In another example, a grommet or similar structure may be used for providing stability, reducing vibration, and for preventing rotation of UV bulb assembly 81. Other structures are envisaged for securing an ozone-generating UV bulb assembly while allowing movement of a shutter that is part of a bulb cover.

UV bulb assembly 81 has a bulb 34 that generates radiation at 185 nm, such radiation producing abundant amounts of ozone when the radiation is exposed to air. In addition, or alternatively, bulb 34 may generate radiation at 253.7 nm for eliminating bioaerosols such as bacteria, viruses, fungi, pathogens, allergens, and others. Further, bulb 34 may be selected to produce germicidal radiation with different proportions (ratios) of ozone production. Such bulbs may be obtained from Light Sources, Inc., of Orange, Conn. In a preferred embodiment of UV lamp assembly 81, bulb 34 is formed of 15 mm hardglass, and is a pre-heat start type lamp 127 mm long, rated for 9,000 hours of bulb life. Actual life depends heavily on operating conditions.

Air purification unit 11 has an upper bulb assembly 82 that, as shown in FIG. 10, is mechanically non-adjustable. Upper bulb assembly 82 is a UV lamp structure having the same general structure and size as UV bulb assembly 81. Upper 
bulb assembly 82 has a ceramic base 33 with a flange 32, and has a ceramic distal end 35, where ceramic base 33 has a body with a diameter less than a corresponding opening 19 of base plate 21 and where a mounting surface 29 of flange 32 abuts base plate 21. A fiber gasket (not shown), having mounting holes aligned with threaded mounting studs at positions 27, 28 and having a center hole larger than the diameter of flange 32 of upper bulb assembly 82, is placed on the mounting studs. Upper bulb assembly 82 is installed into hole 19. An upper bulb clamp 18 is then placed so that the threaded studs pass through corresponding holes in upper bulb clamp 18, and nuts are then tightened onto the threaded studs. The fiber gasket is selected so that upper bulb clamp 18, when secured by tightening of the nuts, is firmly pressed against flange 32 of upper bulb assembly 82 while also providing a cushion for preventing excess tension against upper bulb assembly 82 and for reducing any harmful effects of vibration and/or heavy-handed installation.

Optionally, a lamp retaining clip (not shown) and various spacing and attachment devices may be used for securing a portion of ceramic base 33 to base plate 21. Such a lamp retaining clip may even be formed together with UV lamp 82 by the lamp provider and purchased as a single lamp/clip item. Many other methods and apparatus, such as a flush-mount socket, may be used for mounting upper bulb assembly 82 to base plate 21.

In a preferred embodiment, upper bulb assembly 82 has a same basic structure as UV bulb assembly 81, but generates radiation at 253.7 nm for control of bioaerosols. As shown in FIG. 10, upper bulb assembly 82 has a UV bulb 34 with a length of 406 mm. Air purification unit 11 thereby produces an amount of the 253.7 nm radiation that is not mechanically adjustable within the unit, while also producing a mechanically-adjustable amount of ozone with 185 nm radiation. In this manner, air purification unit 11 is able to reproduce the natural germicidal rays that kill germs, while simultaneously controlling noxious odors created by people, pets, smoke, solvents, carpets, and vinyl coverings. The unit 11 also controls toxins created by pressed-wood products and various other materials that cause human ailments. For example, unit 11 controls allergens by preventing causes and aggravations of allergies.

Air purification unit 11 has two electronic-start type ballasts 14, 15 for respectively supplying electricity to UV bulb assembly 81 and upper bulb assembly 82. For example, ballasts 14, 15 may each have an input at a 115 V line voltage and an output at 230 V with a capacity of 0.42 Amps. The electronic start parameters may be different for ballast 14 compared with ballast 15, corresponding to differences in performance characteristics between UV bulb assembly 81 and upper bulb assembly 82. Ballasts 14, 15 each have four output wires that terminate in corresponding four-pin connectors (not shown). The four-pin connectors each have a female pin structure that mates with pins 37 as shown in FIG. 4B. The two four-wire groups are each protected in respective insulating tubes, such as those made from PVC, plastic, or similar durable and flexible material. The two four-pin connectors may each have four crimp-type female terminals that are crimped onto the ends of the output wires. The crimped terminals are then inserted into appropriate high-voltage insulated connectors. Ballasts 14, 15 each have a corresponding light-emitting diode (LED) 16, 17 that illuminates when the respective ballast is operating normally and providing electrical output for energizing its lamp/bulb. Such ballasts are available from Robertson Worldwide of Blue Island, Ill.

The primary AC input wires of ballasts 14, 15 are connected to a power cord (not shown) using twist-on wire connectors. One or more switches (not shown) may be placed in series with a primary AC feed for one or both of ballasts 14, 15, so that lamps 81 and/or 82 may be energized, for example, only when a controller actuates the particular switch(es). Such a system may utilize an air flow sensor, HVAC fan switch, thermostat, etc. for activating the switch(es). Optionally, one or more switches may be provided for direct user activation of lamps 81 and/or 82. One or (not shown) may be used inline with the primary AC input wires, and/or inline with secondary voltages of ballasts 14, 15. A terminal is attached to the ground wire of the power cord for electrical connection to base plate 21, such as by being secured to threaded stud 27 with a nut.

A box cover 77, as shown in FIG. 9, includes two clear lenses 92 that have a "snap-in" shape for being easily installed. The bottoms of the lenses 92 each have an opening into which a light tube 91 is inserted. When box cover 77 is installed onto two-lamp air purification unit 11, the light tubes 91 transmit the light being emitted from LEDs 16, 17 of ballasts 14, 15 to the respective lenses 92. The user can thereby check the LEDs 16, 17 to determine whether UV bulb assembly 81 and/or upper bulb assembly 82 is currently turned on.

Box cover 77 has an arcuate opening 85 for receiving the extending portion 43 of lever 56 and allowing lever 56 to rotate along with inner tube 46. A spindle 94 is provided in hole 86 of box cover 77. Spindle 94 has a flange type base portion with a diameter larger than hole 86, and a shaft having a diameter smaller than hole 86. The spindle shaft is placed through a nylon washer 95 and then inserted from the inside of box cover 77 through the hole 86. Nylon washer 95 acts as a bushing for allowing rotation of spindle 94. The spindle shaft has a chamfered edge near its distal end, so that when a knob 98 is placed onto the spindle shaft, a set screw (not shown) inside knob 98 may be tightened into the flat surface that is the chamfered edge. When knob 98 is attached to the distal end 42 of extending portion 43 of lever 56, the tightening of the set screw of knob 98 against the chamfered edge acts to align a pointer of knob 98 with respect to the lever 56. Such alignment is effected when attaching box cover 77 to two-lamp air purification unit 11, so that the distal end 42 of extending portion 43 is placed into an alignment hole in the bottom of knob 98, and subsequent tightening of the knob set screw locks the knob 98 in place on lever 56.

Box cover 77 includes extending portions 88 having holes 84 for receiving threaded studs 12 located on opposite ends of base plate 21. Nuts are tightened onto threaded studs 12 for completing the assembly of the air purification unit 11.

Four mounting holes 13 are provided on base plate 21 for installation of two-lamp air purification unit 11 in an air passageway, such as an HVAC duct. An HVAC technician may cut holes in the duct corresponding to UV bulb assembly 81 and upper bulb assembly 82, so that, when two-lamp air purification unit 1 is installed, the outer tube 53 and the exposed UV lamp 82 extend unimpeded into the duct. Care should be taken to avoid breaking exposed UV lamp 82 during installation.

When it suspected that either or both of UV bulb assembly 81 and upper bulb assembly 82 is in need of replacement, such as at a regularly scheduled maintenance period based on rated life of a UV bulb 34 or when one of LEDs 16, 17 is not being illuminated, a user or HVAC serviceperson can easily change the particular bulb assembly. It is essential that the person replacing the bulb assembly first remove the source of primary AC power being supplied to the air purifier 11, such as by use of a breaker box, in-line switch, front panel switch, etc. A disconnect switch (not shown) may be added to the two-lamp air purification unit 11 for breaking a primary AC feed, for example, when cover 77 is removed for servicing. Upon disconnecting power and removing cover 77 and knob 98, the socket is simply pulled away from pins 37 of the appropriate lamp assembly. Then, the corresponding one of upper bulb clamp 18 and/or lower bulb clamp 20 is removed by unfastening the respective pair of nuts. At this point, the old lamp assembly may be removed and a new one installed. The air purifier is then re-assembled and power turned back on.

Bioaerosols are living organisms such as fingi (e.g., mold spores) and germs (e.g., bacteria and viruses). Pathogens are generally known as germs that cause infectious disease. Germs and mold spores may be allergens that cause respiratory reactions and ailments. In most indoor environments, mold spores are the most common bioaerosol. In a residence, a furnace that may include cooling such as central air conditioning provides an optimum environment for the growth and broadcast of bio-aerosols, toxins, and gases that cause unhealthy air environments found in most homes. Because such a furnace presents a collection point for most of the re-circulated air in a building, it offers an ideal location for installing a UV air purification system. By placing the UV air purification unit in the duct-work of an HVAC system, a method and apparatus for germ killing and distribution of ozone may be effected. Although exemplary embodiments described herein relate to installation of an adjustable ozone generator in duct-work, other applications such as a free-standing fan unit are also envisaged.

Figure 11:
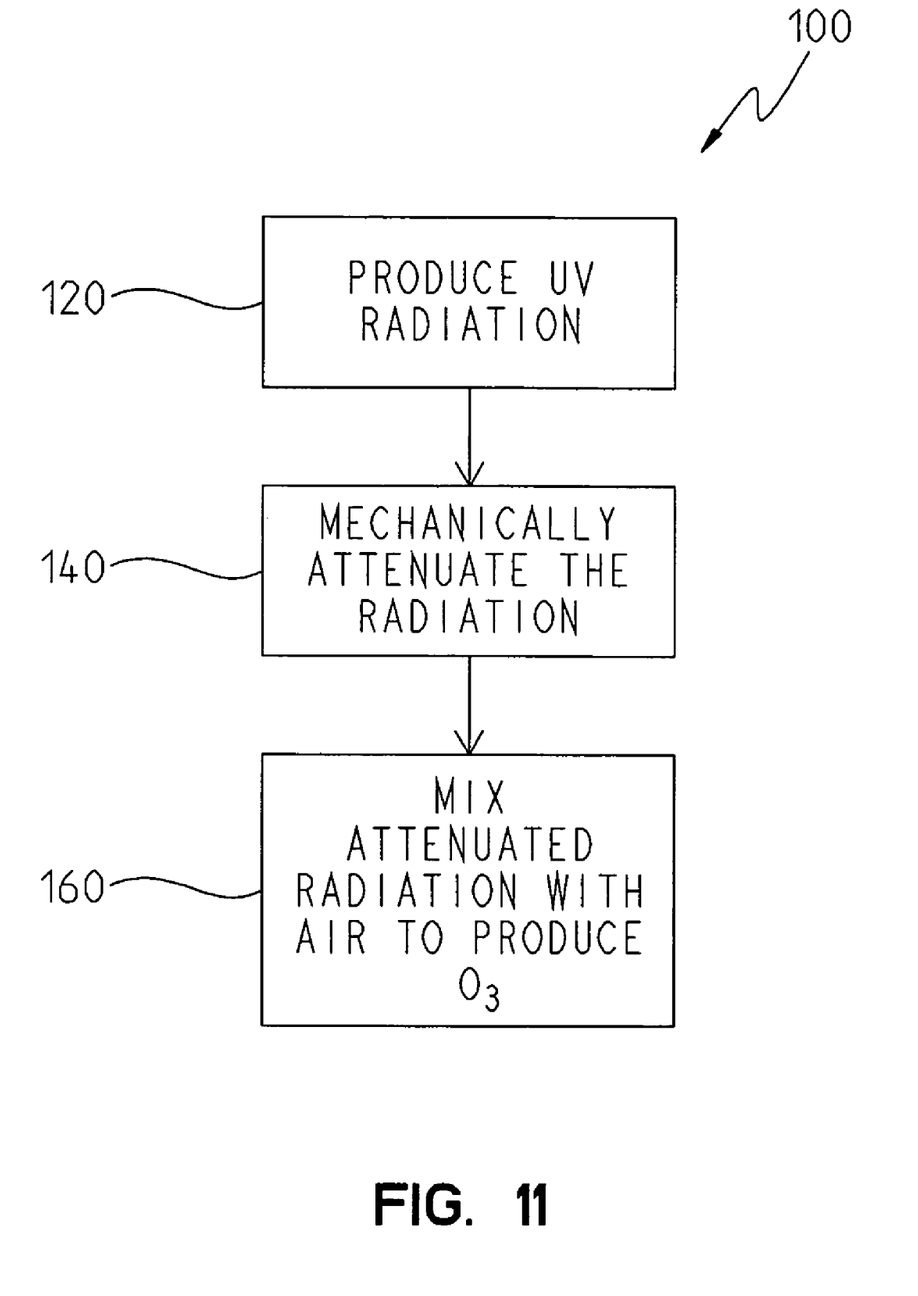
FIG. 11 is a flowchart for an ozone generation method according to an exemplary embodiment of the invention.

FIG. 11 shows an exemplary method 100 according to the invention. In step 120, electric power is provided to a UV lamp that generates ozone at a given rate. Ozone output of UV bulbs may vary widely with changes in airflow, ambient air temperature, pressure, humidity, and many other factors. In step 140, a user adjusts the amount of ozone-generating radiation being released. A manual mechanism is preferably used for the adjusting. In step 160, the UV radiation being released as a result of the mechanical adjusting enters an air flow, thereby creating ozone. As a result, the method allows a user to easily control the amount of ozone by manually adjusting a simple mechanism.

Alternatively, a method may include use of an automated mechanism for automatically and/or controllably adjusting the amount of ozone-generating radiation being released. Such an automated mechanism may include a servo motor or similar electromechanical device such as an actuator that acts as a UV light shutter by driving a mechanism. For example, a so called "smart home" may include remote access, whereby a user can remotely adjust an ozone level, by controllably adjusting an electromechanical device to release more or less WV radiation into an air passageway. Such a system may include logic that activates a blower, fan or other air movement device, and/or timers for energizing a WV lamp for a given period of time. Other applications of a system and method are envisaged for various indoor environments and logistics.

It is noted that method 100 of the invention acts to make a process of generating ozone less efficient. While conventional ozone generators typically try to optimize an efficiency by methods such as channeling or focusing UV radiation, adjusting a plenum and air flow amount through a sterilizer, controlling an ozone amount by using ozone-generating lamps having different lengths and ozone-producing levels, or controlling an ozone amount by placing plastic clips onto a bulb, the present method acts to adjustably attenuate such UV radiation and reduce the resultant ozone-generating efficiency.

While a conventional method may make use of a rheostat or similar device for attempting to adjust a light level being emitted by reducing a voltage being applied to a UV lamp, such a method only serves to operate a light and/or ballast at an improper voltage. This may result in a starting voltage that is not sufficient, creating a scenario where a hazardous voltage is invisible to a service technician or homeowner attempting to determine why a UV bulb is not energized. In addition, such a method causes electrical noise, heat, and accumulation of dirt and dust within a rheostat, service problems, and other difficulties. The present inventor has determined that such conventional problems may be obviated by use of the present invention.

It is important to provide adjustability of the ozone amount. Ozone doesn't mask odors, it oxidizes them. A user of an ozone-generating system will enjoy the sweet smell of clean air after the odors of tobacco smoke, mold, mildew, paint, garbage, litter box, cooking, bathroom odors, and others are removed. In addition, some of the most dangerous gases, which may be odor free, including toxins, are also oxidized. Odors in air generally are gas phase contaminants classified as volatile organic compounds (VOCs). Many people can detect even low part per billion (ppb) concentrations of VOCs in the air, and numerous studies show the human nose to be an excellent gas chromatograph. Certain people may have mild to serious sensitivities to certain or mixed VOCs and their associated odors. In higher concentrations, some VOCs can cause physical discomfort and maladies requiring medical attention. Since a person is able to detect odors, she will know when to adjust the ozone generation system for producing more ozone. Similarly, since ozone has a distinctive odor, she will know when to attenuate the ozone amount.

It is desirable for a homeowner or other user of the present method to conveniently adjust an ozone level. A user may be afraid of adverse effects of excess ozone, whether real or imagined. Although a given amount of ozone will dissipate after 15-20 minutes, such an amount of ozone may cause its own odor that is objectionable to the user. The user can optimize her comfort level, for example, by increasing the amount of ozone after an odor-producing event or while away from home. When concerned with an excess ozone amount, its caustic effects and corresponding health concerns, such as when at home, the user can reduce the ozone level. In addition, the caustic and highly oxidative properties of ozone may be undesirable when there is an excessive level of ozone in many applications such as hospitals, nurseries, senior citizen centers, etc. For example, an amount of ozone in air may be strictly regulated according to threshold limit values, due to its strong oxidative properties and potential harm to humans. In such a case, an institution may utilize various known ozone sensors for assisting a maintenance person in adjusting an ozone level by providing a quantitative value for the ozone amount at a particular location. For example, a hospital may wish to implement a log of ozone readings and corresponding adjustments made to an ozone level at a particular location. Gradations may be printed on the front cover 77 for recording a value for such ozone level adjustments, and various calibration procedures may also be implemented for a controlled environment. Alternatively, a safe level may be assured by selecting a UV bulb having a maximum ozone output (even when the adjustment is set for 'maximum ozone') that is below the required threshold amount.

The present inventor has determined that conventional ozone-type air purifiers are not optimized for adaptation to the particular environment where they are installed. For example, when a given size UV bulb is installed in a residence, conventional devices do not provide the ability to adjust the amount of ozone being produced. Such an ozone-type air purifier may be installed in the ductwork of a residence. For example, a problem exists when a same size ozone-generating air purifier is installed in a 900 square foot home and in a 3000 square foot home. The tenant of the 900 square foot home may object to an excessive amount of ozone, which may itself create an unpleasant or unwanted smell. Although ozone acts to remove odors, an excessive amount may be undesirable. With the present invention, such a tenant is able to easily adjust ozone generation to meet her needs.

Germicidal lamps generating energy at 185 nm create UV emission that produces abundant amounts of ozone in air. Ozone is an extremely active oxidizer, and destroys microorganisms on contact. Ozone also acts as a deodorizer. One of ozone's advantages is that it can be carried by air into places that the UV radiation cannot reach directly. Germicidal lamps themselves may be obtained with different degrees of ozone production. Therefore, an additional level of customization may be implemented with the invention, by choosing a lamp with a particular rated ozone output. For example, an installation technician may select a particular size lamp for a given dwelling size. Upon installation of the air purification system, a user may adjust the ozone level within a corresponding tailored range.

The present invention provides an air purification method that is easy to implement and a system that is inexpensive to purchase and install. An exemplary embodiment implements a system and method for an HVAC system that includes one or more fans and duct-work for moving conditioned air. In most HVAC systems, air is drawn in, filtered, cooled and dehumidified or heated and humidified, and then delivered to a space. Much of this air is recirculated through the HVAC system, although it may be highly beneficial to introduce outdoor air. An HVAC system implementing an ozone type air purifier according to the invention may be installed in offices, hospitals, residential, commercial, industrial and institutional spaces, in modes of transportation such as cars, buses, planes and ships, and anywhere where indoor air is being conditioned.

The germicidal and ozone-producing lamps may have sensitive physical characteristics, such as performance variation due to temperature, humidity, atmospheric pressure, voltage variation, etc. For example, air moving across the lamp may remove heat and lower the lamp's temperature. As a result, materials within the lamp, such as mercury, may begin to condense so that the emission of the germicidal wavelength of 253.7 nm decreases. Since radiation output of a UV bulb can vary for different reasons, adjusting an ozone level is advantageous in maintaining desired ozone and germicidal purification performance in varying conditions.

Conventional systems and methods for removing VOCs may be used in conjunction with the present invention. For example, certain larger applications may lend themselves to a use of various activated carbon filters, liquids for washing VOCs from a gas stream, heat treatment using radiant beds or afterburners to partially catalyze VOCs, photocatalysis in high VOC concentration atmospheres, etc., but these may be less effective and more expensive than the simple methods and systems according to the present invention, without providing corresponding benefit. In addition, such conventional systems may require expensive maintenance, without which they may become less efficient, or even become sources of contaminants.

The present inventor has determined that conventional problems are eliminated by a stationary UV bulb enclosed within a mechanically rotatable shutter-type enclosure. The embodiments described herein were achieved as a result of experimentation and optimization of various factors, including properties of materials and their interaction. While exemplary embodiments have been described, the invention is not thereby limited. For example, any number of UV lamps may be used in any configuration suitable for a given application. UV lamps may produce radiation in various spectra, such as by combining 185 nm light with other wavelengths in one or more individual lamp(s) to achieve optimized performance and controllability while minimizing unnecessary costs. In addition, a mechanism for use with the invention is not limited to structures described above, but may also include any number of individual structures and shapes for effecting adjustment of a level of UV radiation being emitted from an enclosure.

The present invention operates in a manner that is contrary to many conventional devices and methods, which only seek to maximize ozone output by funneling and/or focusing ultraviolet radiation. By comparison, the present invention involves adjusting an ozone-generating radiation amount, which reduces the efficiency of the ozone generation.

Conventional devices may adjust an ozone amount by switching the electric power to the UV lamp according to a predetermined time schedule, such as by using a timer. Additional conventional devices may attenuate an ozone amount by attaching a clip to a UV bulb in order to mask-off a portion of the light being emitted. Such is not useful for adjusting a level of ozone, and may present problems such as decomposition of the clip or safety concerns. Further, as noted above, a conventional device may utilize a rheostat for adjusting a voltage being applied to a UV bulb which creates additional problems since ballasts are designed to operate at a nominal voltage. Still further, conventional attempts to match the amount of ozone being produced with the target area may simply involve using different length UV bulbs having corresponding different UV output amounts. Such does not allow a user to adjust the amount of ozone.

By comparison, the present invention provides a simple solution for adjusting the amount of ozone being generated. By providing a mechanical adjustment of the radiation being emitted for creating ozone, problems of conventional apparatus are eliminated.

While the principles of the invention have been shown and described in connection with specific embodiments, it is to be understood that such embodiments are by way of example and are not limiting. Consequently, variations and modifications commensurate with the above teachings, and with the skill and knowledge of the relevant art, are within the scope of the present invention. The embodiments described herein are intended to illustrate best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method of air purification, comprising:
    providing a UV lamp for producing ozone-generating radiation within a pair of coaxial enclosures, one of the enclosures structured for rotating with respect to the other enclosure;
    providing an opening in each of the enclosures; and
    providing a switch for energizing/de-energizing the UV lamp, switching of the switch corresponding to movement of air through ductwork of a forced-air type indoor environmental control system;

wherein the degree of overlap of the openings effected by the rotating determines an amount of the ozone-generating radiation being outputted via the openings.

2. The method of claim 1, wherein the switch comprises an air flow sensor.

3. The method of claim 1, wherein the switch comprises a fan switch.

4. The method of claim 1, further comprising:
providing a shaft affixed at its proximal end to the rotating one of the enclosures; and
providing a knob affixed to a distal end of the shaft, where rotation of the knob effects rotation of the rotating enclosure and correspondingly changes the degree of overlap.

5. The method of claim 1, further comprising providing an electrical connector for supplying electricity to the UV lamp, the electrical connector being removable and independent of the enclosures.

6. A method of air purification, comprising:
providing a UV lamp for emitting ozone-producing radiation;
providing an enclosure for covering the UV lamp, the enclosure having a mechanically-adjustable opening for changing an amount of the radiation being emitted from the enclosure, the enclosure consisting essentially of a pair of cylinders, one of the cylinders being structured for rotating respecting the other cylinder;
providing an HVAC duct as an ozone-creating passageway for receiving the radiation being emitted from the enclosure; and
mounting the UV lamp and enclosure into the HVAC duct.

7. The method of claim 6, further comprising providing a switch for energizing/de-energizing the UV lamp.

8. The method of claim 7, wherein the switch comprises an air flow sensor.

9. The method of claim 7, wherein the switch comprises a fan switch.

10. The method of claim 6, further comprising providing an electrical connector for supplying electricity to the UV lamp, the electrical connector being removable and independent of the enclosure.

11. A method of air purification, comprising:
providing a UV lamp for producing ozone-generating radiation within a pair of coaxial enclosures, one of the enclosures structured for rotating with respect to the other enclosure;
providing an opening in each of the enclosures;
providing a base;
providing a first lamp holder structured for securing the UV lamp to the base; and
mounting the base onto an HVAC duct;
wherein the degree of overlap of the openings effected by the rotating determines an amount of the ozone-generating radiation being outputted via the openings.

12. The method of claim 11, further comprising:
providing a germicidal lamp; and
providing a second lamp holder structured for securing the germicidal lamp to the base.

13. The method of claim 11, further comprising:
providing a shaft affixed at its proximal end to the rotating one of the enclosures; and,
providing a knob affixed to a distal end of the shaft, where rotation of the knob effects rotation of the rotating enclosure and correspondingly changes the degree of overlap.

14. The method of claim 13, wherein the shaft extends in parallel to longitudinal axis of the lamp.

15. A method of purifying air in a surrounding airflow, comprising:
providing a UV lamp that generates ozone-producing radiation when energized, the UV lamp having a longitudinal axis;
providing an airflow-preventing enclosure completely covering the UV lamp except for a single, variable opening portion of the airflow-preventing enclosure, thereby substantially preventing the airflow from flowing through the airflow-preventing enclosure, the airflow-preventing enclosure comprising:
a first cylinder having a cylinder sidewall, having a first window in the first cylinder sidewall, and being fixedly disposed about the longitudinal axis; and,
a second cylinder having a second cylinder sidewall, having a second window in the second cylinder sidewall, and being rotatably disposed about the longitudinal axis;
providing a shaft affixed at its proximal end to the second cylinder, the shaft extending in parallel with the longitudinal axis, where rotation of the shaft effects rotation of the second cylinder and correspondingly changes an amount of overlap of the first and second windows, such overlap effecting the variable opening portion, the overlap having a tapered shape; and
mounting the airflow-preventing enclosure within ductwork of a forced-air type indoor environmental control system.

* * * * *